(12) United States Patent
Coulange et al.

(10) Patent No.: US 10,524,935 B2
(45) Date of Patent: *Jan. 7, 2020

(54) SURGICAL INSTRUMENTATION ASSEMBLY FOR POSITIONING AN ANKLE PROSTHESIS

(71) Applicant: Integra LifeSciences Corporation, Plainsboro, NJ (US)

(72) Inventors: Vincent Coulange, Lyons (FR); Sophie Genna, Venon (FR); Yann Brunnarius, Chatuzange le Goubet (FR); Emmanuel Lizee, Saint Ismier (FR); Christophe Perineau, Grenoble (FR); Michel Bonnin, Lyons (FR); Christiaan Coetzee, St. Paul, MN (US); Jean-Alain Colombier, Balma (FR); Thierry Judet, Ville d'Avray (FR); Mark Myerson, Baltimore, MD (US)

(73) Assignee: INTEGRA LIFESCIENCES CORPORATION, Plainsboro, NJ (US)

( * ) Notice: Subject to any disclaimer, the term of this patent is extended or adjusted under 35 U.S.C. 154(b) by 329 days.

This patent is subject to a terminal disclaimer.

(21) Appl. No.: 15/400,557

(22) Filed: Jan. 6, 2017

(65) Prior Publication Data

US 2017/0112638 A1 Apr. 27, 2017

Related U.S. Application Data

(63) Continuation of application No. 13/669,321, filed on Nov. 5, 2012, now Pat. No. 9,539,115.
(Continued)

(30) Foreign Application Priority Data

Feb. 6, 2012 (FR) ..................................... 12 51091

(51) Int. Cl.
*A61F 2/46* (2006.01)
*A61B 17/17* (2006.01)
(Continued)

(52) U.S. Cl.
CPC ............ *A61F 2/4684* (2013.01); *A61B 17/15* (2013.01); *A61B 17/1739* (2013.01);
(Continued)

(58) Field of Classification Search
CPC . A61B 17/1775; A61B 17/15; A61B 17/1739; A61F 2002/4205; A61F 2002/4207; A61F 2/4202
(Continued)

(56) References Cited

U.S. PATENT DOCUMENTS 5,320,529 A 6/1994 Pompa
5,947,973 A * 9/1999 Masini ................. A61B 17/154
606/87
(Continued)

FOREIGN PATENT DOCUMENTS

EP 2589354 A1 5/2013
FR 1251091 1/1961
(Continued)

OTHER PUBLICATIONS

Search Report issued in French Application No. 1251091 dated Apr. 25, 2012.

*Primary Examiner* — Jessica Weiss
(74) *Attorney, Agent, or Firm* — Middleton Reutlinger

(57) ABSTRACT

In order to position an ankle prosthesis including a tibial implant and a talus implant provided with a talo-calcaneal anchoring keel, the invention proposes a surgical instrumentation assembly including: a tibial phantom (60) of the tibial implant, adapted so as to be attached to the tibia (T) of a patient, and an aiming guide (80) adapted for setting into
(Continued)

place an instrumentation element (90) through the talus (A) and the calcaneus (C) of the patient, along an axis (Z-Z) for implanting the talo-calcaneal anchoring keel, the tibial phantom and the aiming guide mechanically cooperating with each other to restrict movement of the tibial phantom and the aiming guide relative to each other along vertical and medio-lateral directions, wherein the aiming guide is configured to guide placement of the instrumentation element.

24 Claims, 17 Drawing Sheets

Related U.S. Application Data

(60) Provisional application No. 61/555,593, filed on Nov. 4, 2011.

(51) Int. Cl.
*A61B 17/15* (2006.01)
*A61F 2/42* (2006.01)

(52) U.S. Cl.
CPC ........ *A61B 17/1775* (2016.11); *A61F 2/4202* (2013.01); *A61F 2002/4205* (2013.01); *A61F 2002/4207* (2013.01)

(58) Field of Classification Search
USPC ...... 606/79–80, 83, 86 R–88, 102, 184–185; 623/20.32–20.34, 902, 908, 21.18
See application file for complete search history.

(56) References Cited

U.S. PATENT DOCUMENTS

| | | |
|---|---|---|
| 6,663,669 B1 | 12/2003 | Reiley |
| 6,926,739 B1 | 8/2005 | O'Connor et al. |
| 7,534,246 B2 | 5/2009 | Reiley et al. |
| 9,539,115 B2 | 1/2017 | Coulange et al. |
| 2006/0142870 A1* | 6/2006 | Robinson ............... A61B 17/15 623/21.18 |
| 2007/0173947 A1 | 7/2007 | Ratron et al. |
| 2010/0057216 A1 | 3/2010 | Gannoe et al. |
| 2010/0305572 A1 | 12/2010 | Saltzman et al. |
| 2012/0130376 A1* | 5/2012 | Loring ................ A61B 17/025 606/80 |

FOREIGN PATENT DOCUMENTS

| | | |
|---|---|---|
| GB | 2445146 | 7/2008 |
| GB | 2479899 | 11/2011 |
| WO | 2009158522 | 12/2009 |
| WO | WO-2009158522 A1 * | 12/2009 ........... A61B 17/025 |

* cited by examiner

SURGICAL INSTRUMENTATION ASSEMBLY FOR POSITIONING AN ANKLE PROSTHESIS

CROSS-REFERENCE TO RELATED APPLICATIONS

This application is a continuation of and claims priority and benefit under 35 U.S.C. § 120 to copending U.S. patent application Ser. No. 13/669,321, filed on Nov. 5, 2012, which claims priority and benefit under 35 U.S.C. § 119(e) to U.S. Provisional Patent Application Ser. No. 61/555,593, filed on Nov. 4, 2011, and claims foreign priority to French Patent Application No. 1251091, filed on Feb. 6, 2012, which the entire contents of the aforementioned applications are incorporated herein by reference in their entireties for all purposes.

TECHNICAL FIELD

The present invention relates to a surgical instrumentation assembly for positioning an ankle prosthesis.

BACKGROUND

Placement of an articular prosthesis at the ankle of a patient during a surgical operation, typically from an anterior approach path, requires preparation notably by resections, of the lower end of the tibia, as well as often the upper end of the talus of the patient, in order to permanently fix thereon the tibia and talus implants belonging to the ankle prosthesis. In practice, once the bone preparations are carried out, the surgeon frequently resorts to phantoms of prosthetic implants, allowing the surgeon to make sure that these preparations are suitable and that additional bone cutting or additional resurfacings are not necessary. These phantoms are not necessarily of the same shape as the corresponding implant.

Sometimes, a patient may be fitted with an initial fitted ankle prosthesis, and the initial implantation may be revised subsequently; in the case of a revision, the talar implant is often provided with a talo-calcaneal anchoring keel, which may be sufficiently long for stabilizing the talus implant facing both the talus and the calcaneus of the patient. This being said, this type of ankle prosthesis with a long keel may of course be positioned as a first intention prosthesis, notably if the bones of the foot are highly damaged. It is understood that the positioning instrumentation for an ankle prosthesis with a long keel should allow the surgeon to prepare the talus and the calcaneus accordingly, so that these bones are ready to receive the aforementioned long keel in an ad hoc housing. Further, in spite of all the care which the surgeon may provide in handling such instrumentation, notably with a significant intervention time, the risks are not negligible that the preparation of the aforementioned housing might be not satisfactory, in the sense that the implantation of the talus component resulting from this does not allow good subsequent articular cooperation with the tibial component attached to the tibia.

SUMMARY

Embodiments of the present invention include a surgical instrumentation assembly for positioning an ankle prosthesis with a talus implant provided with a talo-calcaneal anchoring keel, an instrumentation assembly which allows the surgeon to ensure satisfactory implantation positioning between the tibial implant and the talus implant, notably for reasons of stability and longevity of the ankle prosthesis.

A surgical instrumentation assembly for positioning an ankle prosthesis according to embodiments of the present invention includes a tibia implant and a talus implant provided with a talo-calcaneal anchoring keel, the instrumentation assembly including a tibial phantom of the tibial implant, adapted for attachment to the tibia of a patient, and an aiming guide, adapted for setting into place an instrumentation element through the talus and the calcaneus of the patient along an axis for implanting the talo-calcaneal anchoring keel, wherein the tibial phantom and the aiming guide mechanically cooperate with each other to restrict movement of the tibial phantom and the aiming guide relative to each other along vertical and medio-lateral directions, wherein the aiming guide is configured to guide placement of the instrumentation element.

According to some embodiments of the present invention, the tibial phantom and the aiming guide are mechanically coupled so that the vertical and medio-lateral positioning of the tibial phantom on the tibia correspondingly forces vertical and medio-lateral positioning of the aiming guide. In this way, the placement by the aiming guide of a talo-calcaneal instrumentation element such as a pin or the like, is positioned relative to the tibial phantom when the latter is attached to the tibia in the same configuration as the one in which the tibial implant of the ankle prosthesis will then be attached. Once this instrumentation element is thus placed through the talus and the calcaneus, it is intended to be used by the surgeon for preparing the talus and the calcaneus to receive the anchoring keel of the talus implant of the prosthesis, this preparation therefore being reliably and accurately positioned with respect to the tibial phantom fixed to the tibia.

In practice, the aforementioned instrumentation element is placed by the aiming guide while the surgeon sets the ankle of the patient in a preferential configuration, notably by setting the foot at 90° with respect to the leg of the patient in the sagittal plane. Thus, the implantation of this element and therefore the implantation of the anchoring keel of the talus implant are achieved by means of the instrumentation according to embodiments of the invention, by taking into account the implantation of the tibial implant and of the aforementioned preferential configuration of the ankle.

The subsequent articular performances of the thereby implanted ankle prosthesis are remarkable because of the satisfactory relative positioning of the tibia and talus implants, this positioning being easily obtained rapidly by the surgeon during the positioning operation by the instrumentation according to embodiments of the present invention.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
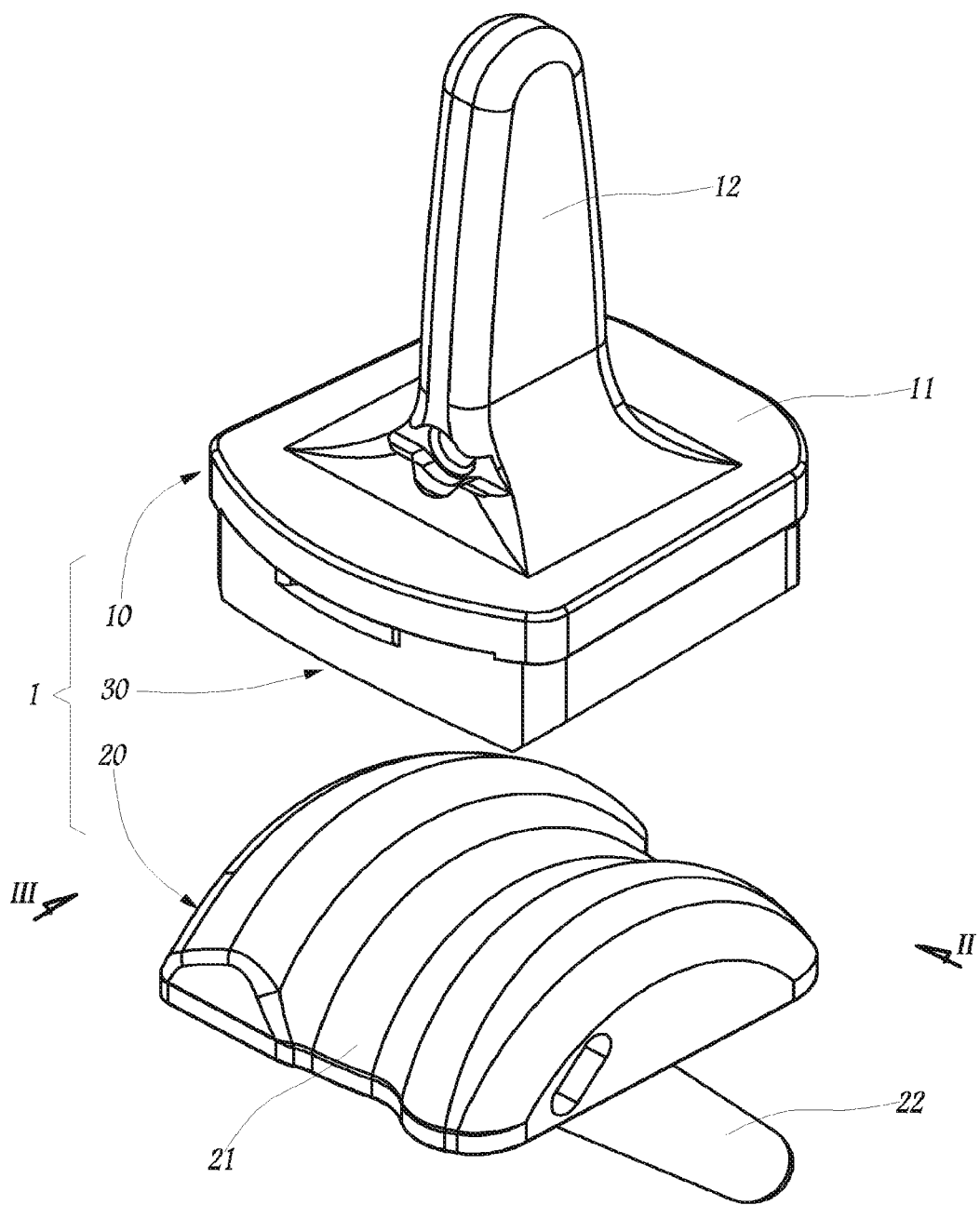
FIGS. 1 to 3 illustrate an ankle prosthesis, FIG. 1 being an exploded perspective view and FIGS. 2 and 3 corresponding to elevational views along the arrows II and III of FIG. 1 respectively.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
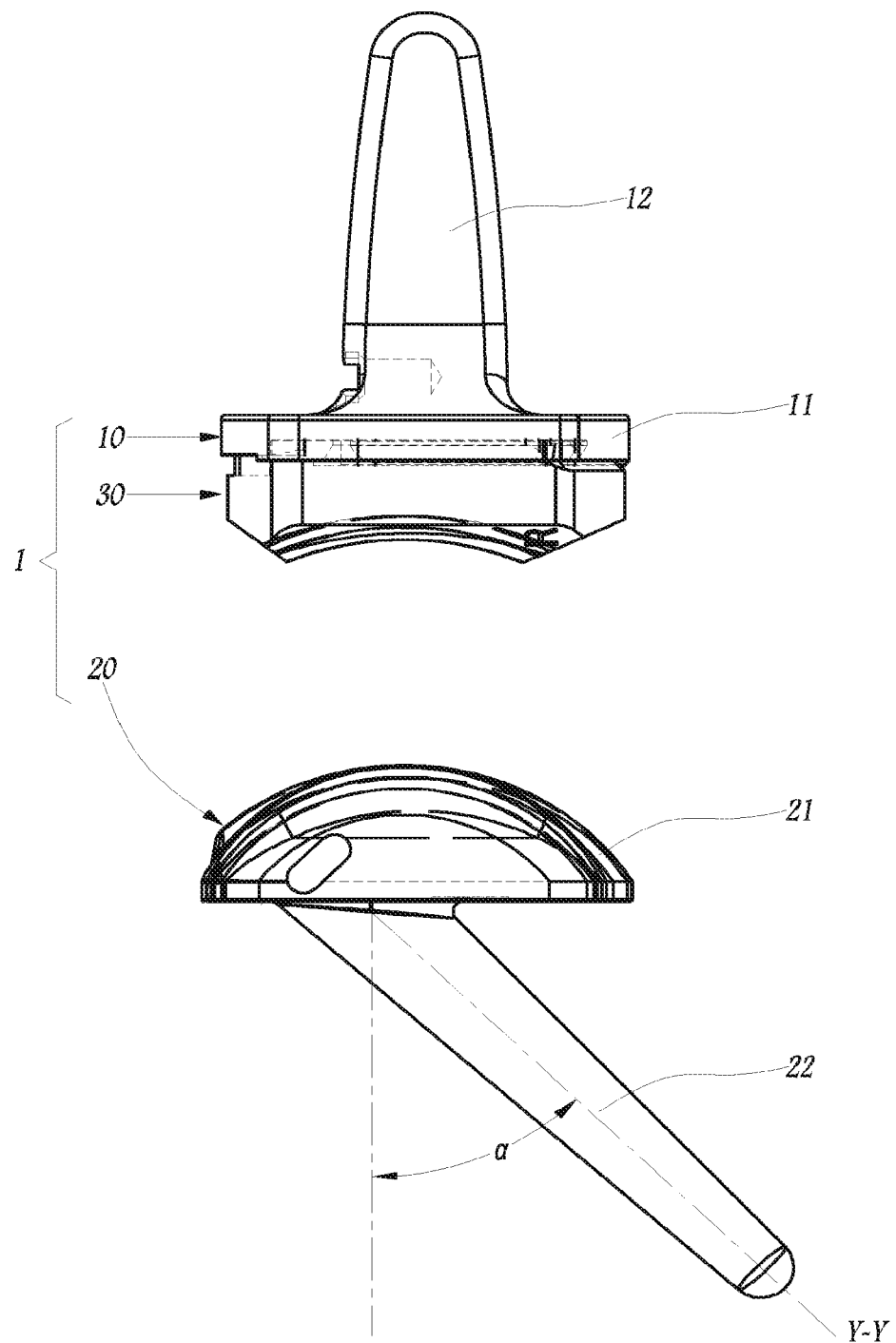
Figure 3:
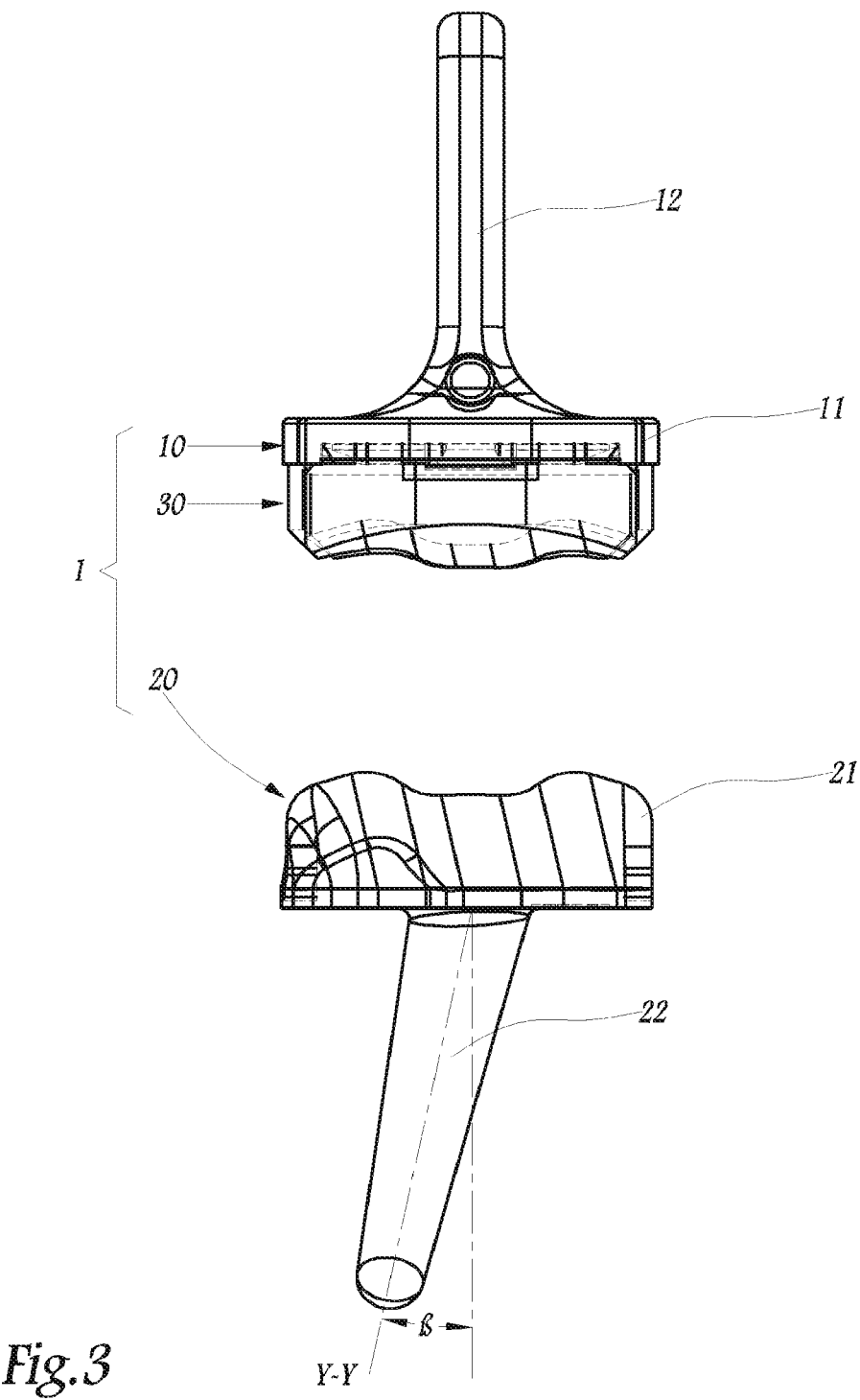

In FIGS. 1 to 3, an example of an ankle prosthesis 1 is illustrated. This prosthesis includes three distinct components to be implanted at the joint of an ankle of a human being, in this case, for the example considered in the figures, a right ankle of such a human being. These components are a tibia implant 10, a talus implant 20 and a prosthetic shoe 30.

For convenience, the following of the description is oriented relatively to the bones of an ankle in their anatomic position, i.e. the term of "posterior" or "rear", "anterior" or "front", "right", "left", "upper", "lower", and the like, are understood with respect to the ankle of a patient standing on his/her feet on a substantially horizontal surface. Also the term of "sagittal" corresponds to a direction in the antero-posterior direction, vertically on the middle line of the ankle, while the "front plane" corresponds to a vertical plane perpendicular to the sagittal plane of the ankle.

The tibial implant 10 includes a plate 11 to be attached to the lower end of the right tibia of a patient, after suitable preparation of this end. For this purpose, the plate 11 is, on its upper side, made in a same material with a bone anchoring sagittal stem 12 intended to be cemented with respect to the tibia. As an alternative not shown, bone anchoring means, other than the sagittal stem 12, may be contemplated for the plate 11 from the moment that they efficiently immobilize the tibia implant 10 at the lower end of the tibia.

On its lower side, the plate 11 is secured to the upper face of the shoe 30. In practice, various embodiments are contemplated with respect to the securing interface, not visible in detail in the figures, either fixed or mobile, between the plate 11 and the shoe 30.

The talus implant 20 includes a main block 21 to be attached to the upper end of the right talus of a patient, for example through an anchoring keel 22 extending downwards from the lower side of the block 21. The keel 22 has a significant longitudinal dimension, in the sense that, in operation, the keel 22 is provided so as to continuously extend through the whole right talus of the patient and through at least one portion of the right calcaneus of the patient. Further, as this is well visible in FIGS. 2 and 3, keel 22 extends from the lower side of the block 21 with a specific tilt, related to the fact that the keel 22 is configured so as to extend into bone portions of greater bone mass and higher stress resistance of the talus and of the calcaneus, notably with purposes of stabilization of the keel towards the bones. The benefit of this arrangement is related to the fact that the talus of the patient may, upon positioning of the implant 20, either be of a poor bone quality, or only be present in a small amount, or having been at least partly altered beforehand, in particular following the removal of a talus implant from a first-time fitted ankle prosthesis, implanted earlier in the patient to be operated, which moreover justifies in the latter case that the prosthesis 1 be described in some embodiments as a "revised prosthesis".

According to one embodiment of the present invention, the keel 22 has an essentially frusto-conical outer surface, centered on a geometrical axis Y-Y which extends along the longitudinal direction of the keel 22 and which forms an axis for implantation of this keel in the talus and the calcaneus. Also as a non-limiting example and independently of the frusto-conical outer shape of the keel 22, the central longitudinal axis Y-Y of this keel is inclined relatively to the normal to the lower side of the main block 21, more generally relatively to a vertical anatomic direction, by forming, in a sagittal plane like in FIG. 2, an angulation α and forming in a front plane like in FIG. 3, an angulation β. The angulations α and β may have respective variable values, depending on the anatomy of the patient: in particular, according to some embodiments of the present invention, the angulation α has the value from about 40 to 55° and the angulation β has the value from about 0 to 15°.

On its upper side, the block 21 delimits an articular surface intended to cooperate with a conjugate articular surface which is delimited on the lower side of the shoe 30. In practice, the profile of the aforementioned articular surfaces is not a limitation of the present invention and will therefore not be further described: in any case, by articular cooperation with the upper side of the block 21 and the lower side of the shoe 30, the ankle prosthesis 1 advantageously provides kinematics close to those of the natural joint of the ankle.

A surgical method will be described hereafter, aiming at implanting the ankle prosthesis 1, it being understood that the relevant prosthesis is only a non-limiting illustrative example of the method and of the surgical instruments used for implanting this prosthesis. In other words, the method and the instruments detailed hereafter may be used for implanting ankle prostheses of very diverse structures, for example for which the tibia and/or talus implants consist of several parts assembled to each other, of metal, plastic and/or ceramic nature.

Figure 4:
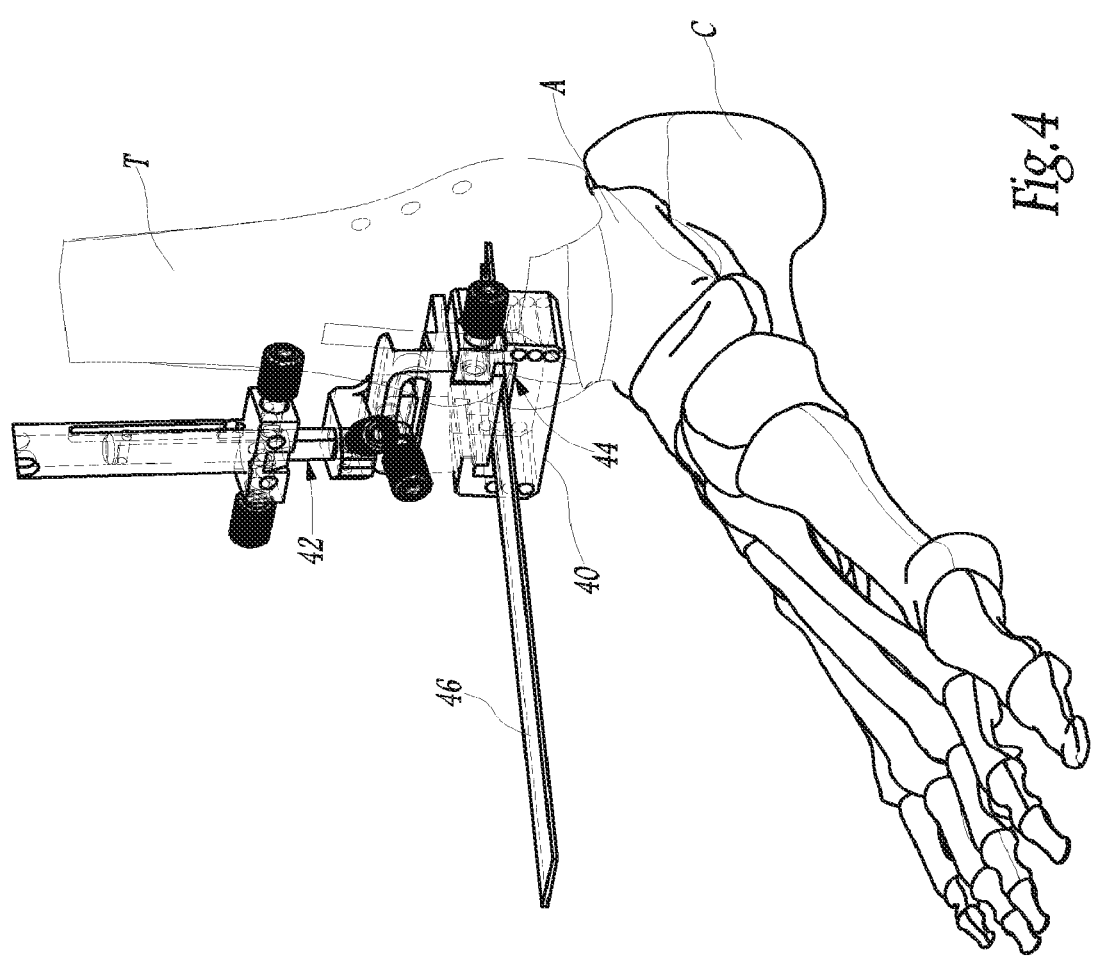
FIG. 4 is a perspective view of the ankle of a patient illustrating a first step for preparing this ankle with view to positioning of the prosthesis of FIGS. 1 to 3, this first preparation step being carried out by a corresponding portion of an exemplary embodiment of an instrumentation assembly according to embodiments of the present invention.

In a first operating step, which is illustrated in FIG. 4, the tibia T begins by being prepared at the right ankle of the patient. For this purpose, the surgeon uses a first cutting block 40 which, in the relevant exemplary embodiment here, is attached onto the tibia T via a positioning guide 42: this positioning guide 42 is designed in order to be fixedly pressed on the tibia T, notably on its epiphysis and/or its anterior tuberosity, while allowing adjustment of at least certain characteristics of the positioning of the cutting block 40, supported by the positioning guide 42, relatively to the tibia T. In particular, the positioning guide 42 provides the possibility of adjusting the position of the cutting block 40 along the longitudinal direction of the tibia T and/or the angular position of the cutting block 40 around an antero-posterior axis and/or the position of the cutting block 40 along a medio-lateral axis.

Alternatively, the positioning guide 42 described above may be replaced with unadjustable means for immobilizing the cutting block 40 on the tibia T, typically in the form of one or several bone anchoring pins, directly and fixedly binding the cutting block and the bone material of the tibia, according to embodiments of the present invention.

The cutting block 40 delimits a slot 44 for accepting a bone cutting mechanism, into which the surgeon introduces and guides for example a cutting blade 46 so as to resect the lower end of the tibia T along a corresponding tibial cutting plane.

Figure 5:
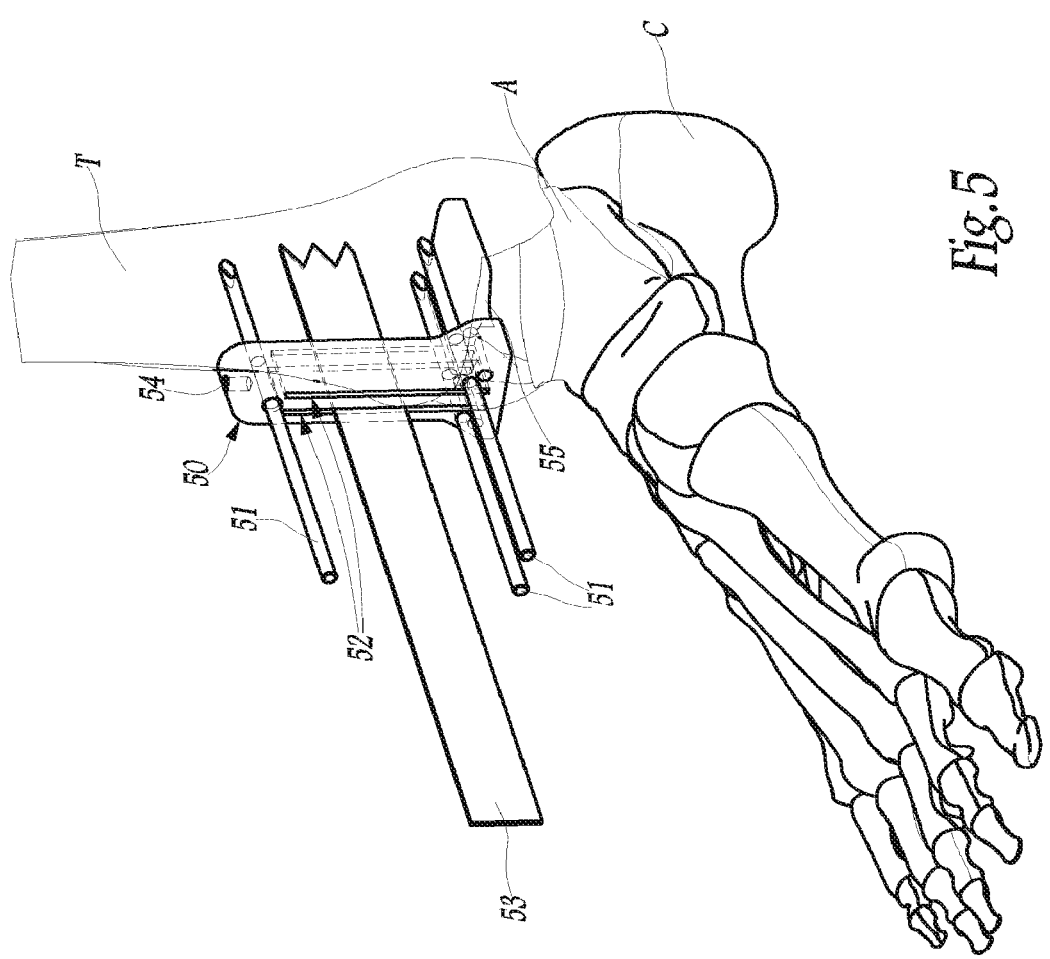
FIG. 5 is a view similar to FIG. 4, illustrating a second step for preparing the ankle with a corresponding portion of the instrumentation, according to embodiments of the present invention.

Before proceeding to the second operating step described and shown in FIG. 5, an optional intermediate step, not shown, includes resecting the upper end of the talus A of the ankle of the patient, by then forming a corresponding talus cutting plane. In particular, as a non limiting example, the tibial and talus cutting planes are substantially parallel to each other when the foot of the patient is positioned at 90° relative to the patient's leg. In practice, such resection of the talus A is often not necessary within the scope of a revision surgical operation in the sense that the bone preparation of the talus, which had been carried out earlier with the purposes of implanting a first-time fitted ankle prosthesis, has already given rise to the making of such a talus cutting plane and is therefore generally sufficient for positioning the ankle prosthesis 1. This having been said, if need be, the surgeon has the option of using a cutting blade or a similar mechanism for resecting the upper end of the talus A, for example by introducing and guiding this cutting blade in the slot of a cutting block which is similar to the cutting block 40 described above and which may be borne by the positioning guide 42.

More generally, before proceeding to the second operating step described hereafter with reference to FIG. 5, other secondary operations for bone preparation of the lower end of the tibia T and/or of the upper end of the talus A may be carried out in order to have on these ends cutting planes suitable for positioning the ankle prosthesis 1. For example, such additional steps may include the elimination, on the bone surfaces corresponding to these cutting planes, of possible osteophytes or residual materials.

In a second operating step, illustrated in FIG. 5, a window may be made in the anterior face of the tibia. To do this, the surgeon uses a second cutting block 50 which the surgeon immobilizes on the tibia T, notably with pins 51 introduced into the tibia along a globally antero-posterior direction. This block 50 delimits two slots 52, which extend parallel with each other along a vertical direction and into each of which the surgeon introduces a bone cutting mechanism, in this case a cutting blade 53 as shown in FIG. 5, so as to cut into the bone material of the tibia T, two substantially vertical grooves, which open only onto the anterior face of the tibia, according to embodiments of the present invention.

In practice, before immobilizing the block 50 on the tibia T with the pins 51, the surgeon carefully positions this block 50 so that both grooves made in the tibia extend parallel to the longitudinal direction of the tibia T. To do this, as an example, a localizing element 54 is provided on the cutting block 50 so that this localizing element 54 is aligned on the tibial crest in the front plane relative to the angle, while being parallel with this crest in a sagittal plane, when the cutting block is suitably positioned relative to the tibia. Additionally, the cutting block 51 may be provided with a palette 55 designed so as to be flattened upwards against the tibial cutting plane. Such palette 55 may protrude on the rear face of the cutting block 51, according to embodiments of the present invention.

Figure 6:
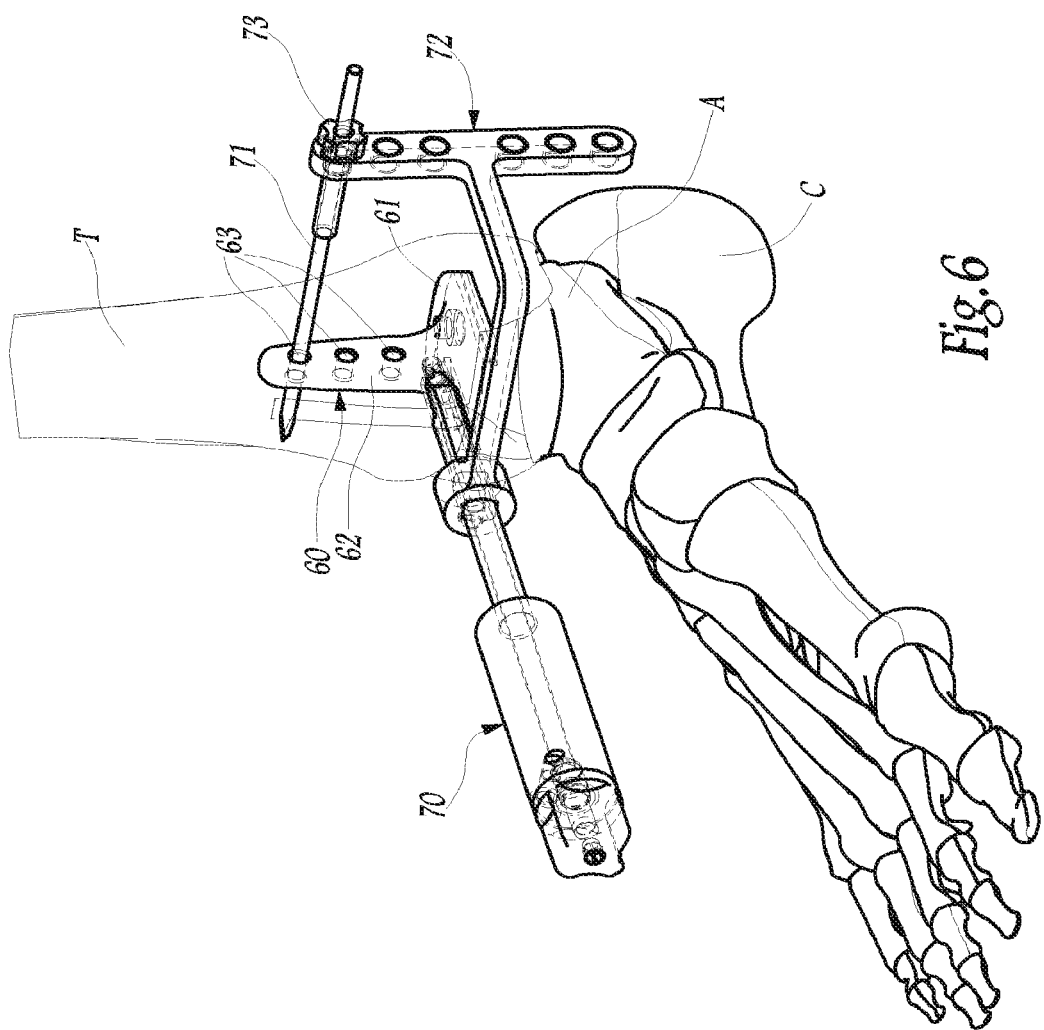
FIG. 6 is a view similar to FIGS. 4 and 5, illustrating a third step for preparing the ankle with a corresponding portion of the instrumentation, according to embodiments of the present invention.

At the end of the second operating step, the cutting block 50 is disengaged and, with an osteotome, in particular a Poirier osteotome, the segment of bone material subsisting between both grooves made in the anterior face of the tibia T may be detached from the remainder of the tibia, thereby clearing a window through the tibia T. As shown in FIG. 6, the aforementioned tibial window opens both onto the anterior face of the tibia and onto the tibial sectional plane. If need be, the walls delimiting the aforementioned tibial window are reworked, for example with rasps provided for this purpose.

Figure 7:
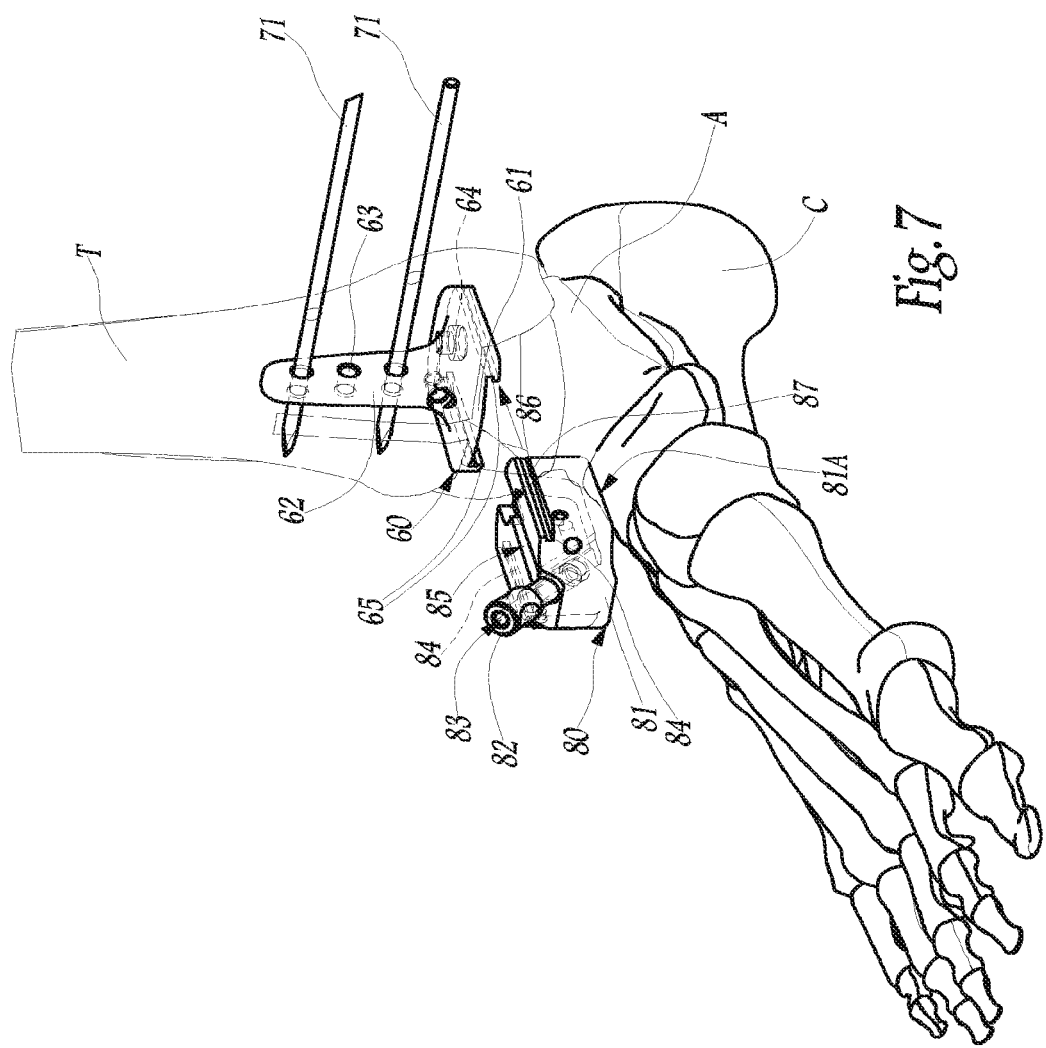
FIGS. 7 to 9 are views similar to FIGS. 4 to 6, respectively illustrating successive movements of a fourth step for preparing the ankle with corresponding portions of the instrumentation, according to embodiments of the present invention.
Figure 10:
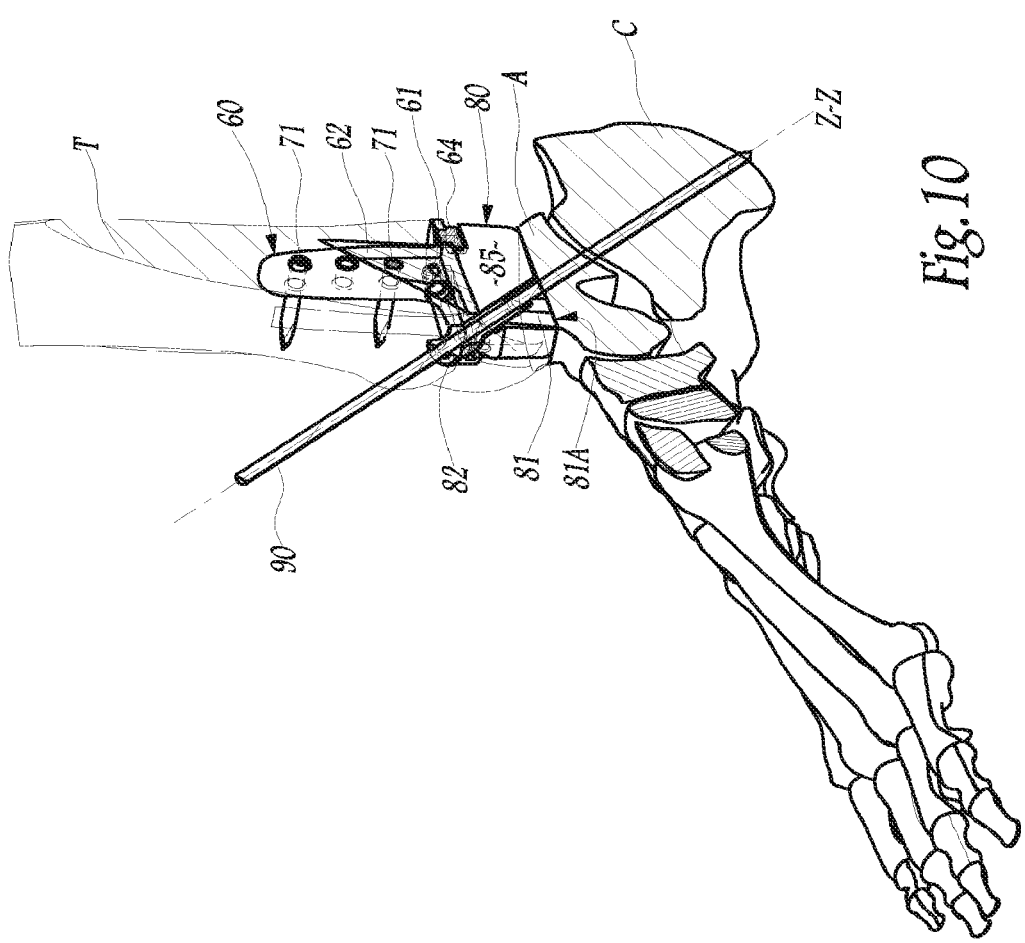
FIG. 10 is the same view as that of FIG. 9, with a partial sectional view along the plane X indicated in FIG. 9, according to embodiments of the present invention.

In a third operating step, shown in FIG. 6, a test tibial implant, in other words a tibial phantom 60 of the tibial implant 10, may be set into place on the tibia T. This tibial phantom 60 includes a main plate 61, which has a peripheral contour geometrically similar to that of the plate 11 of the tibial implant 10 and for which the upper side has the same arrangement as that of the plate 11, i.e. the plate 61 is provided with a protruding sagittal stem 62 geometrically similar to the stem 12 of the tibial implant 10. Further, the stem 62 of the tibial phantom 60 delimits through-holes 63 for receiving a pin for attachment to the tibia. On its lower side, the plate 61 has a planar surface which, as indicated in dotted lines in FIG. 6, and as partly visible in FIGS. 7 and 10, is provided with, in the central region of this lower planar surface, a protruding bulge 64 which, in the relevant exemplary embodiment shown, is made in the same material with the remainder of the plate 61; and each of the opposite, medial and lateral edges of this lower planar surface, a slide 65, which extends along an antero-posterior direction from the front end of the plate 61 towards the rear end of the latter and which, in the relevant exemplary embodiment here, has an overall U profile, the respective recesses of the U profiles of both slides 65 being directed towards each other along a medio-lateral direction.

In order to set into place the tibial phantom 60, the surgeon manipulates it with a grip 70, the distal end of which is adapted to be removably attached to a dedicated area of the tibial phantom 60, this area being located, in one non-limiting example, at the base of the anterior side of the stem 62. It is understood that by displacing the grip 70, the surgeon is thus able to insert the tibial phantom 60 into the ankle joint of the patient via an anterior route, more specifically by inserting the stem 62 into the inside of the aforementioned tibial window, while flattening the upper face of the plate 61 against the lower sectional plane of the tibia T.

In practice, the surgeon adjusts the antero-posterior position of the tibial phantom 60 relative to the tibia T by correspondingly displacing the grip 70 while, along the vertical direction, the surgeon makes sure that the plate 61 is maintained pressed upwards against the lower sectional plane of the tibia T. The surgeon may be assisted for this by retractors or similar equipment, according to embodiments of the present invention.

Once the surgeon decides that the tibial phantom 60 is properly positioned on the tibia T, the surgeon fixes it into position with pins 71 introduced through the lower end of the tibia T, by passing each pin through one of the through-holes 63 of the stem 62. Advantageously, the insertion of these pins 71 is guided by an aiming guide 72, which is borne by the grip 70 and which bears a piercing barrel 73 for guiding each pin 71 along the respective central axis of the through-holes 63.

Once the tibial phantom 60 is attached on the tibia T by the pins 71, the grip 70 and the aiming guide 72 are disengaged therefrom.

As an option, a control with an image intensifier may then be applied for confirming the proper positioning of the tibial phantom 60 with respect to the tibia T.

Figure 8:
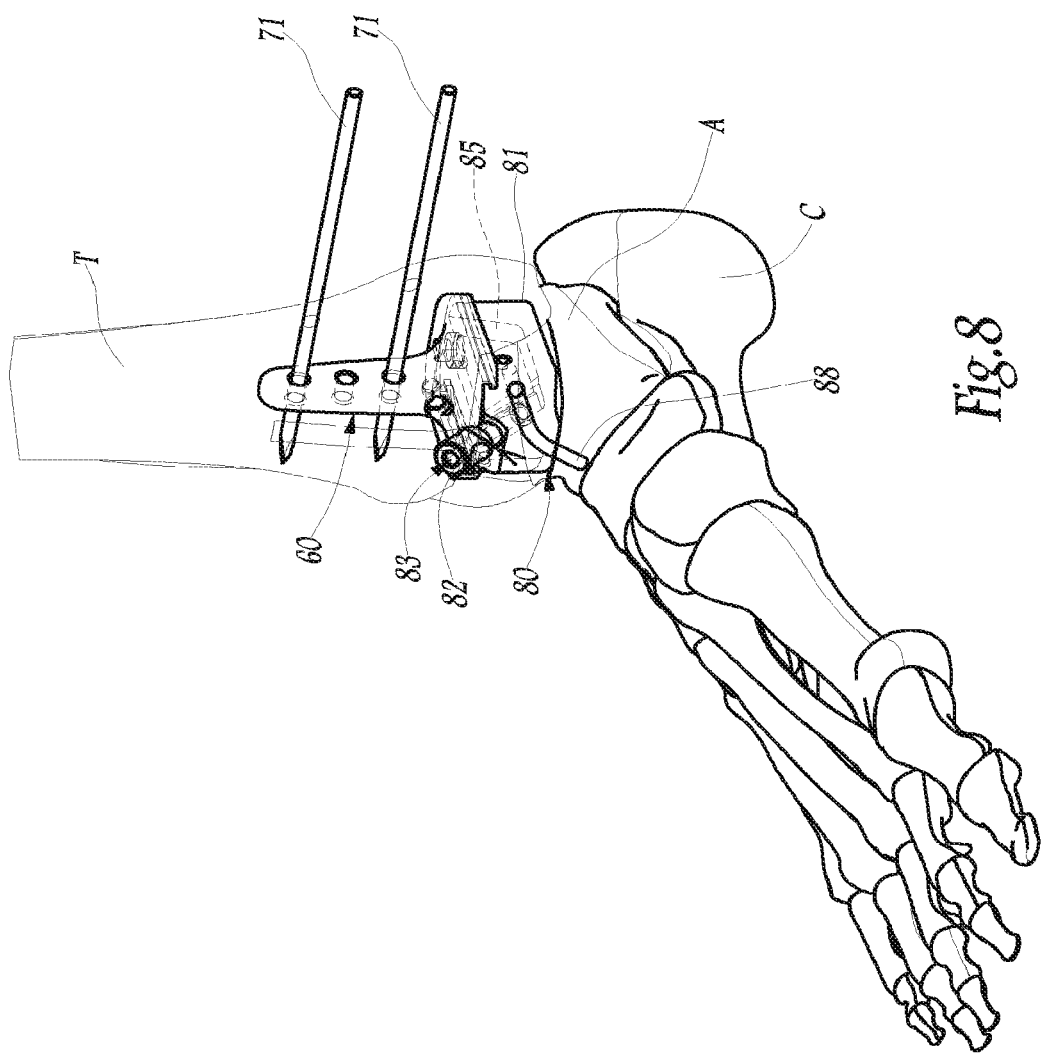

In a fourth operating step, which is illustrated by FIGS. 7 to 10, the talus A and the calcaneus C may be prepared with view to positioning the implantation of the talo-calcaneal keel 22 of the talus implant 20. To do this, the surgeon uses an aiming guide 80 which, as well visible in FIGS. 7 and 10, includes a main body 81, as well as a piercing barrel 82 which delimits a bore 83 for letting through a pin and which is removably borne by the body 81. The body 81 of the aiming guide 80 is dimensioned so as to be received in an interposed way, along the vertical, between the plate 61 of the tibial phantom 60 attached to the tibia T and the upper sectional plane of the talus A, as shown in FIG. 8. More specifically, the upper side of the main body 81 is provided, on each of these opposite, medial and lateral edges, with a slider 84 which extends along an antero-posterior direction. These sliders 84 are adapted so as to be respectively engaged complementarily into the slides 65 of the tibial phantom 60 so as to reversibly assemble the tibial phantom 60 and the aiming guide 80 according to an antero-posterior sliding link.

The slides 65 and the sliders 84 are dimensioned, to within functional tolerances, in order to limit, or even make substantially zero the relative displacements between the tibial phantom 60 and the aiming guide 80 along both the vertical direction and the medio-lateral direction. In other words, the antero-posterior sliding link between the tibial phantom 60 and the aiming guide 80 represents the only degree of freedom of displacement between these components. In other words, the vertical and medio-lateral positioning of the tibial phantom 60 on the tibia T accurately constrains or restricts the vertical and medio-lateral positioning of the aiming guide 80.

Further, as partly illustrated in dashed lines in FIG. 7 and as shown in FIG. 10, the main body 81 of the aiming guide 80 delimits, in its median region, a slot 85, which is open on the outside while opening both onto the opposite, upper and lower faces of the body 81 and on the rear face of the body 81, while the slot 85 is closed at the front face of the body 81 by a front wall of this body. Slot 85 is arranged so as to removably attach thereto the piercing barrel 82 so that the bore 83 of the latter opens downwardly into the inside of the slot 85. Thus, as shown in FIG. 10, the central longitudinal axis of the bore 83 crosses the body 81 while extending into the inside of the slot 85, by going from the lower end of the piercing barrel 82 as far as the lower face of the main body 81. The plane of FIG. 10, which corresponds to the plane noted as X in FIG. 9, is a plane containing the central axis of the bore 83 and parallel to the sliding direction of the sliding link between the tibial phantom 60 and the aiming guide 80, this plane forming a middle plane, notably a plane of symmetry for the slot 85, according to embodiments of the present invention.

Within the scope of the method for positioning the ankle prosthesis 1, the aiming guide 80 is manipulated by a surgeon, if necessary, via a grip (not shown), such that the body 81 of the aiming guide is inserted under the tibial phantom 60, by sliding the aiming guide 80 against the tibial phantom by engagement of the sliders 84 with the slides 65, as indicated by the arrow 86 in FIG. 7. The slid position of the aiming guide 80 relative to the tibial phantom 60, in other words the relative antero-posterior positioning between the aiming guide and the tibial phantom, is adjusted by the surgeon. Accordingly, several approaches may be used. Indeed, this adjustment may be left to the entire discretion of the surgeon. According to some embodiments of the present invention, preferential or extreme positioning is advantageously provided to the surgeon, by abutment, along the antero-posterior direction, between the bulge 64 of the plate 61 of the tibial phantom 60 and the main body 81 of the aiming guide 80, this body 81 delimiting a housing 87 for complementary reception of the bulge 64. For example, FIGS. 8 to 10 illustrate the abutment of the bulge 64 in this housing 87, according to embodiments of the present invention.

Figure 9:
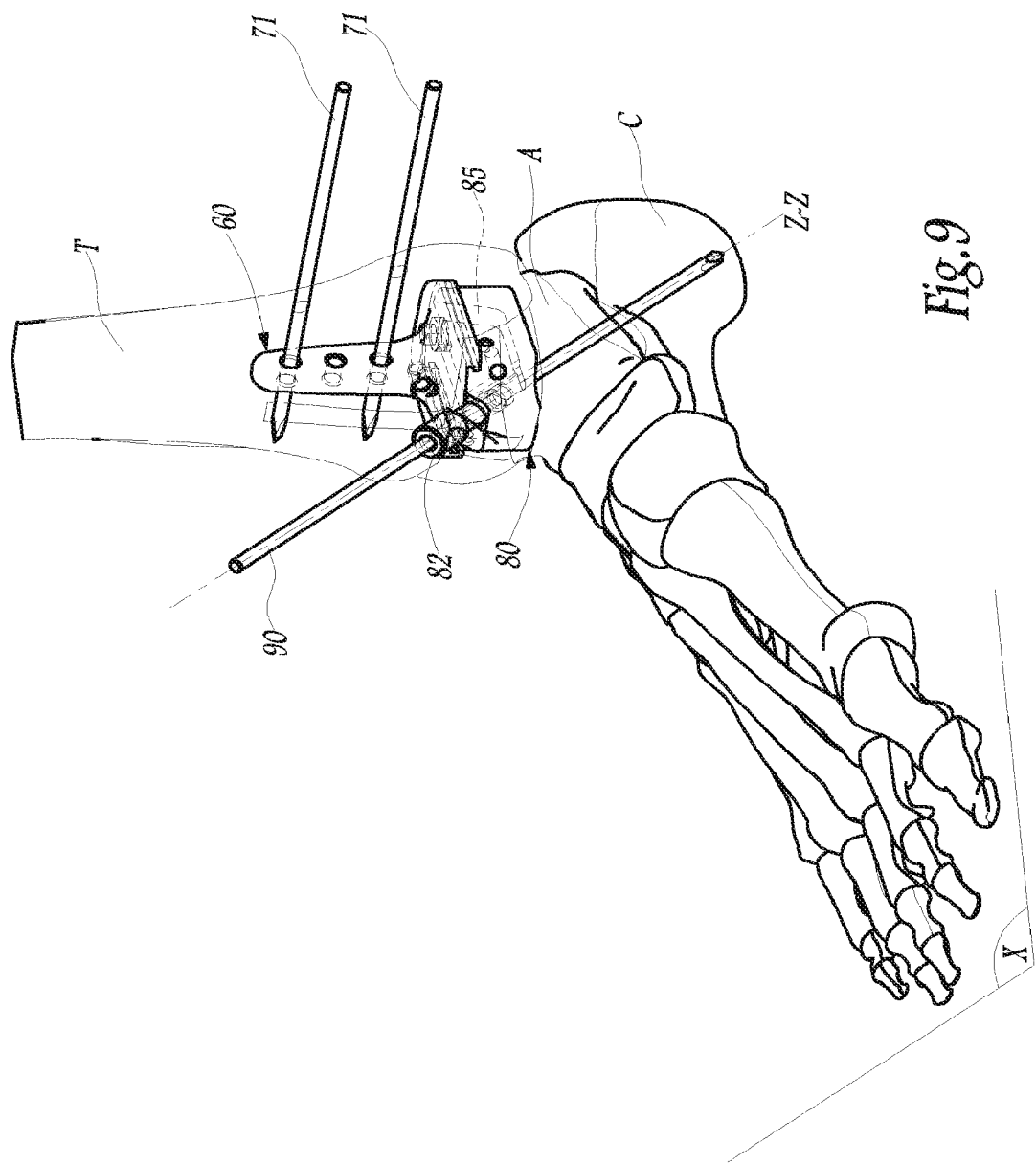

In any case, once the relative positioning between the aiming guide 80 and the tibial phantom 60 is adjusted according to the desire of the surgeon, and while maintaining the foot of the patient at 90° relative to the patient's leg, the surgeon introduces a pin 90 into the piercing barrel 82, this pin being driven towards the rear of the foot, while being guided by the bore 83 in a centered way on the axis of the latter, successively through the slot 85, through the whole talus A and through at least one portion, or even the totality of the calcaneus C, as illustrated in FIGS. 9 and 10. As explained below, this talo-calcaneal pin 90 determines the implantation positioning of the talus implant 20, for example by determining an implantation axis Z-Z of the keel 22 of the talus implant 20.

As an option, just before putting the pin 90 into place, the aiming guide 80 may be used by the surgeon for checking and if necessary adjusting the alignment of the joint of the ankle while the foot of the patient is maintained at 90° relative to the patient's leg. To do this, the aiming guide 80 is provided with a predetermined raised portion or localization mark of the position of the aiming guide 80 with respect to at least one anatomic singularity of the talus A, such as the talonavicular joint. Moreover, in FIG. 8, the main body 81 bears as an advantageous optional arrangement such a raised localization portion 88 on which the surgeon may align the talonavicular joint of the foot. The localization portion 88 may also be referred to as a visual indicator 88, according to embodiments of the present invention.

At the end of this fourth operating step, while the pin 90 is left in place through the talus A and the calcaneus C, and while the tibial phantom 60 is left in place on the tibia T, the surgeon totally disengages the aiming guide 80. More specifically, the surgeon detaches the piercing barrel 82 relative to the main body 81 and has this piercing barrel slide along the pin 90 towards the front end of the latter, until it is removed from the pin. Next, the surgeon has the main body 81 slide forwards (i.e. anteriorly) with respect to the tibial phantom 60: the benefit of the presence of the slot 85 is thus understood as permitting disengagement of the main body 81 without the main body 81 interfering with the pin 90 left in place, this slot 85 being dimensioned accordingly, notably with respect to its tilt relative to the upper and lower faces of the main body 81, as well as with respect to its mediolateral width, according to embodiments of the present invention.

Figure 11:
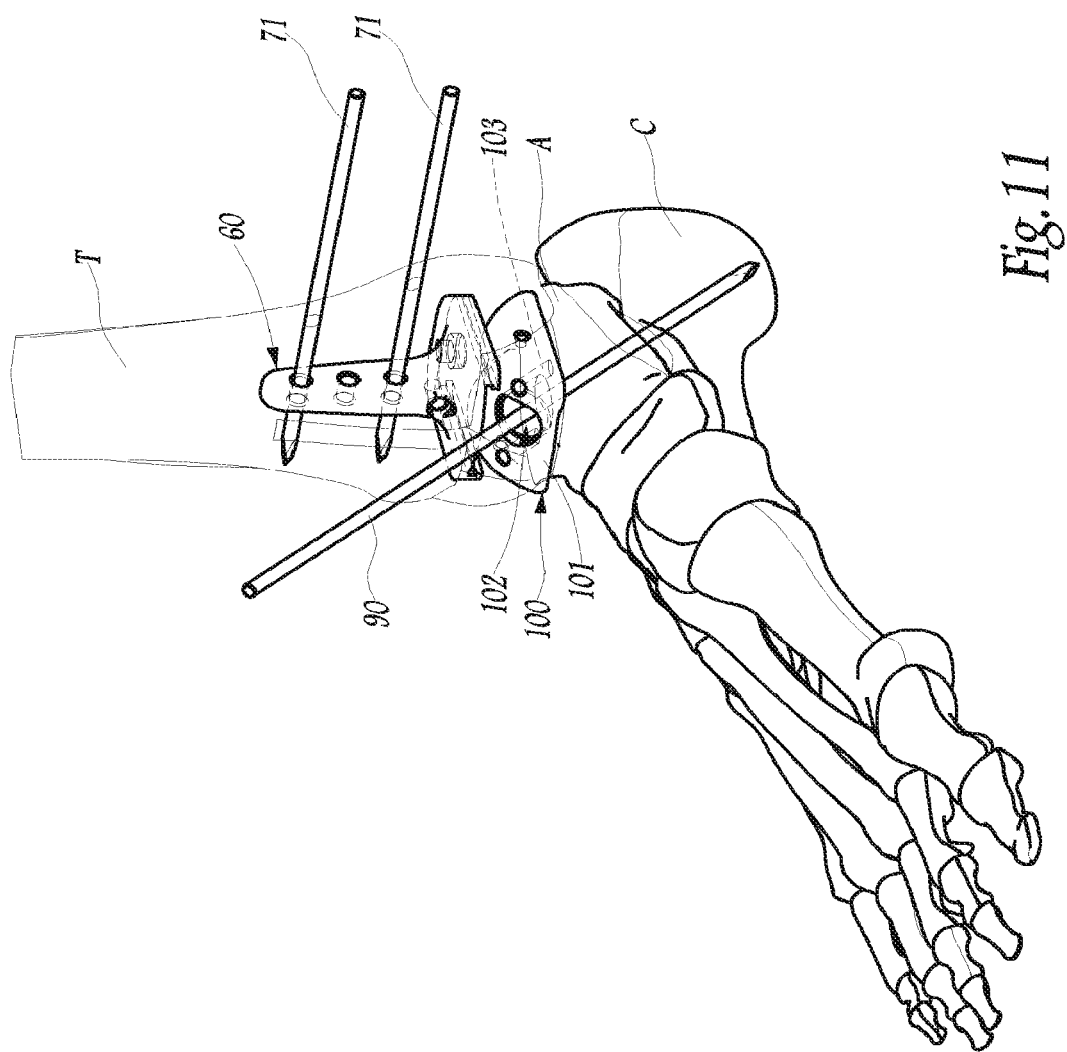
FIGS. 11 to 13 are views similar to FIGS. 4 to 9, respectively illustrating the successive moments of a second step for preparing the ankle with corresponding portions of the instrumentation, according to embodiments of the present invention.
Figure 12:
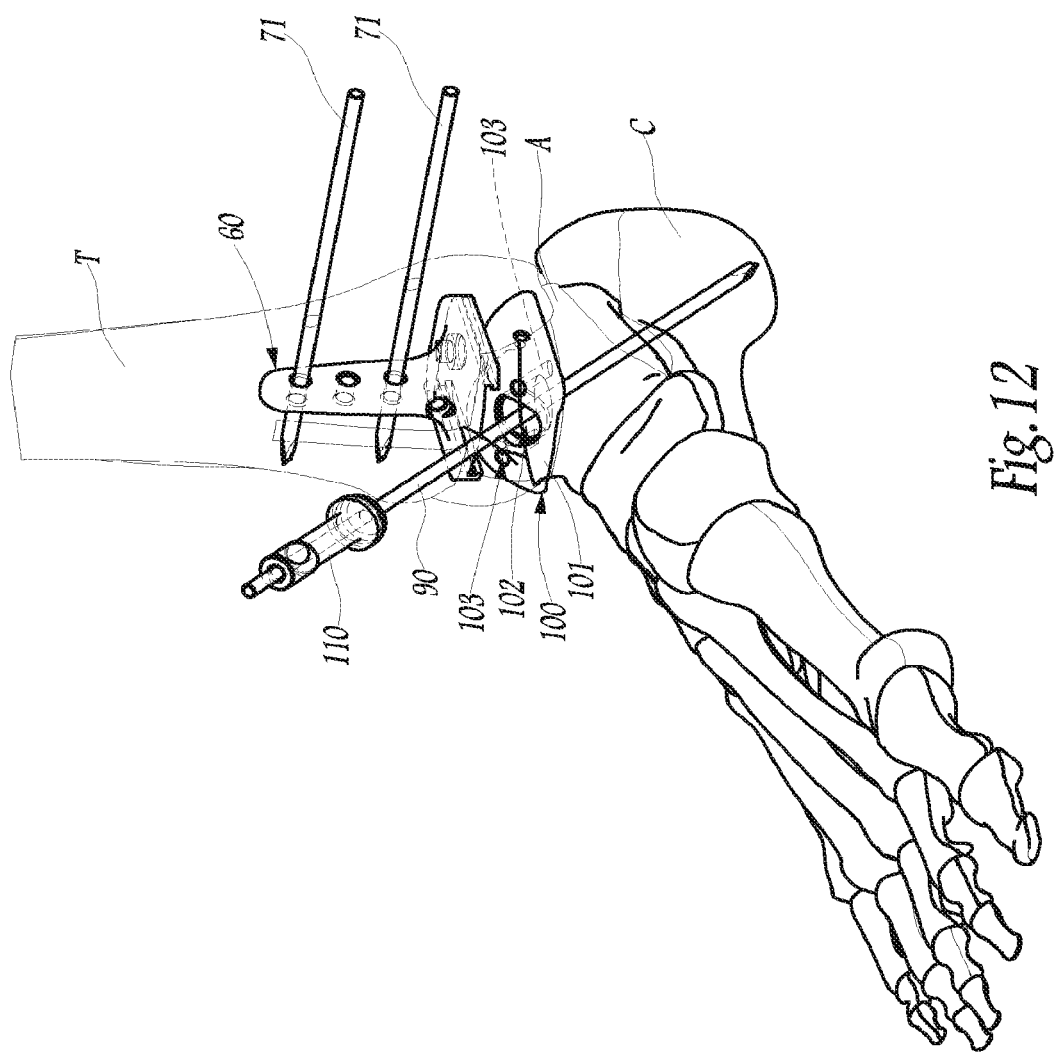
Figure 13:
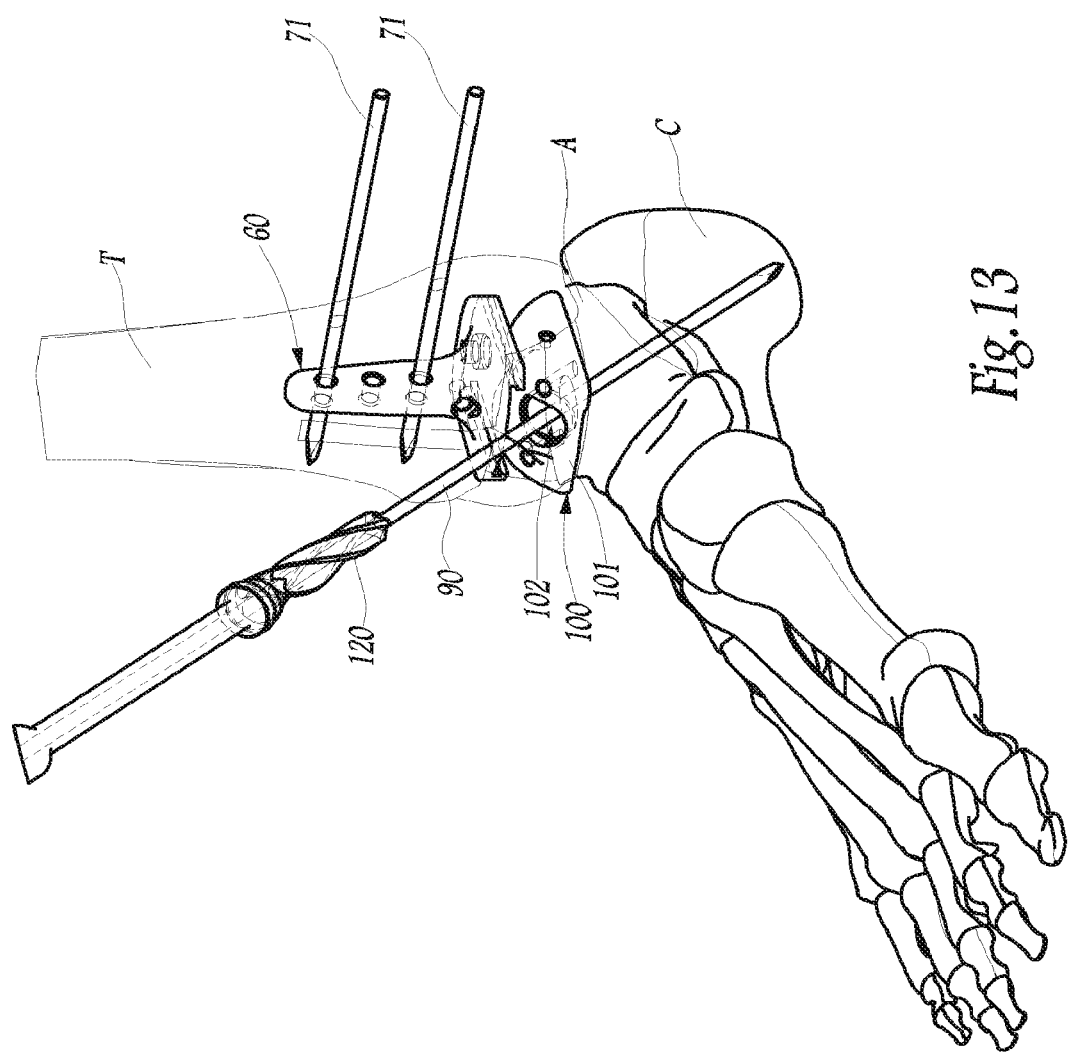

In a fifth operating step illustrated by FIGS. 11 to 13, the talus A and the calcaneus C may be pierced in order to produce in these bones a receiving housing mating the keel 22 of the talus implant 20. To do this, as illustrated in FIG. 11, a test talus component, in other words a talus phantom 100, is set into place in an interposed way between the tibial phantom 60 and the talus A. This talus phantom 100 includes a main block 101 delimiting a lower planar surface which has a peripheral contour geometrically similar to that of the lower surface of the main block 21 of the talus implant 20. The block 101 may be set into place on the talus A, by flattening it against the upper sectional plane of this talus, in other words in a configuration similar to the one which the talus implant 20 will occupy at the end of the intervention.

The talus phantom 100 may thus set into place while the pin 90 is left in place through the talus A and the calcaneus C. Therefore, the main block 101 is provided with a through-hole 102, which connects the upper and lower sides of the block 101 and inside which the pin 90 is axially engaged. In other words, the talus phantom 100 is slid over the pin 90 until it flattens the lower face of its main bulk 101 against the sectional plane of the talus A. Some freedom of tilt of the main block 101 relative to the pin 90 may be left, which accounts for why the diameter of the through-hole 102 is significantly larger than the external diameter of the pin 90. This arrangement may benefit from the surgeon's use of a centering device 110, which, as illustrated in FIG. 12, may be slid over the pin 90 while being adjusted on the outer diameter of the latter, until it is laid out, by adjustment in a radially interposed way between the pin 90 and the main block 101, at the through-hole 102 of the latter. Once the centering device 110 occupies the through-hole 102, the positioning of the talus phantom 100 is constrained specifically with respect to the pin 90, with the block 101 of this phantom being held downwards bearing against the upper sectional plane of the talus. The position of the talus phantom 100 may then be set with respect to the talus, by attaching the main block 101 with two added pins (not shown) introduced into dedicated through-holes 103 of the main block 101.

As an alternative (not shown), the through-hole 102 opens onto the front of the block 101, which forms an open slot at one end to facilitate the setting into place of the pin 90 in this slot, in the sense that at any intermediate level of the pin, the pin may be laterally engaged into the aforementioned slot. Unless the width of the aforementioned slot is limited to the diameter of the pin 90, which may prove to be a constraint in terms of peroperative manipulations, the subsequent use of the centering device 110 remains relevant, according to embodiments of the present invention.

As an option, before continuing the progression to the fifth operating step, a control with an image intensifier may be used to confirm the proper alignment of the tibial 60 and talus 100 phantoms.

After having removed the centering device 100 by backing it out along the pin 90, according to a reverse procedure relative to its initial installation, the talus A and the calcaneus C are pierced (e.g. drilled, reamed, and the like) in order to produce in these bones a mating receiving housing for the keel 22 of the talus implant 20. This piercing may be achieved with the pin 90 left in place through the talus A and the calcaneus C, by using the pin 90 as a guiding support along which is slid at least one bone piercing tool 120, such as a cannulated milling tool or a reamer, as illustrated in FIG. 13. Moreover, several of these piercing tools may be used successively for widening and/or reworking the shape of the successive bone cavity. In each case, the main block 101 may form an abutment, along the longitudinal direction of the pin 90, for these piercing tool(s) 120: in this way, the central longitudinal axis of the pin 90 determines the central axis Z-Z around which is made the cavity for receiving the anchoring keel 22, while the abutment of the piercing tool(s) 120 against the talus phantom 100 determines the depth of this cavity.

Figure 14:
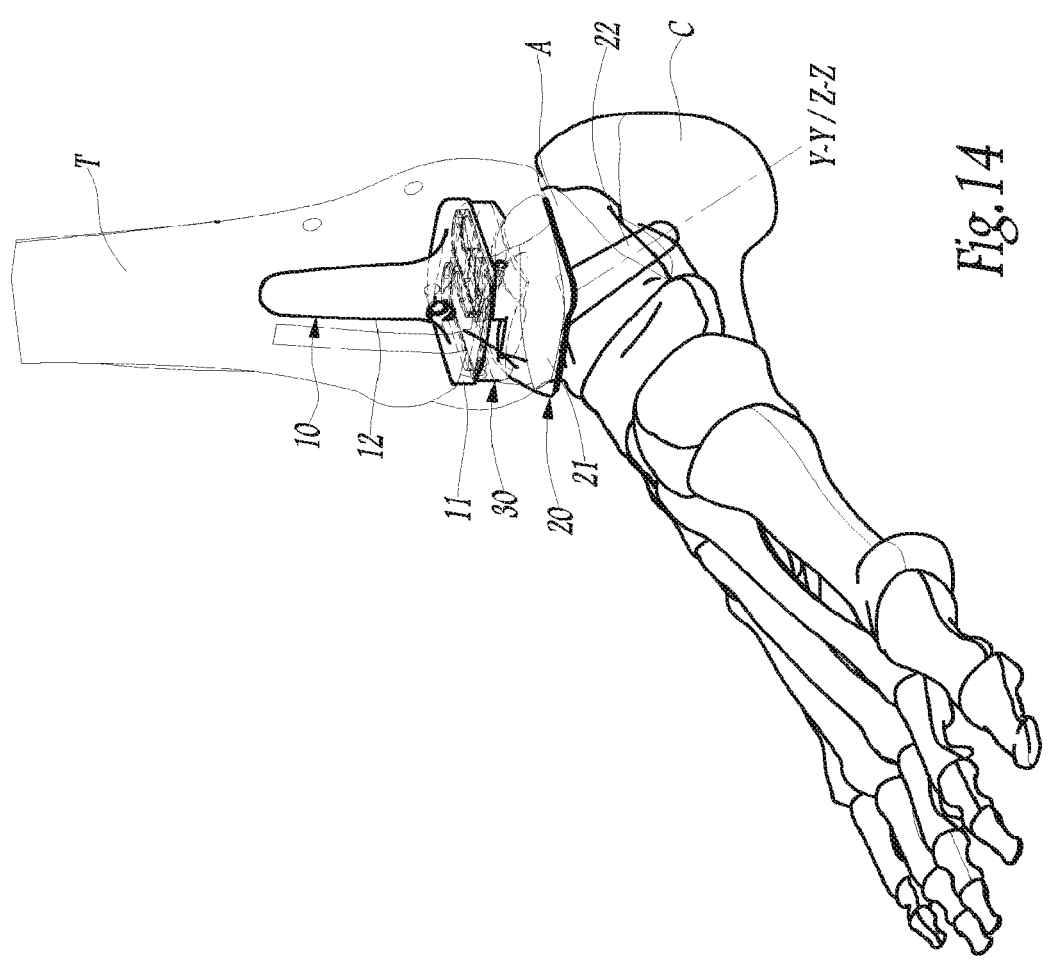
FIG. 14 is a view similar to FIGS. 4 to 9 and 11 to 13, illustrating the implantation of a prosthesis of FIGS. 1 to 3 at the ankle having been prepared by the instrumentation, according to embodiments of the present invention.

At this stage of the surgical operation, the tibia T, the talus A and the calcaneus C are ready to receive the tibia 10 and talus 20 implants of the prosthesis 1, as described hereafter with reference to FIG. 14. Optionally, before setting these implants 10 and 20 into place, tests may be conducted by the surgeon with the tibial phantom 60, the talus phantom 100 and one or several phantoms, not shown, of the shoe 30 for adjusting the vertical spacing between the lower end of the tibia T and the upper end of the talus A and thereby re-establishing anatomical separation between them, as well as with test rods, not shown, passed through the main block 101, via the through-hole 102, in order to check the proper depth of the housing made through the talus and the calcaneus. Once these tests are completed, the pin 90, as well as the pin 71 are removed and the phantoms 60 and 100 are cleared.

The surgical operation ends with the setting into place of the tibia 10 and talus 20 implants, as illustrated in FIG. 14. In particular, the talus implant 20 is mounted on a specific grip, not shown, in order to be put into place on the talus A, by engaging its keel 22 into the housing made through the talus A and the calcaneus C and by aligning its axis Y-Y on the axis Z-Z for implanting it along this axis. Next, the tibia implant 10, on which the prosthetic shoe 30 has been attached beforehand, is, for example via a specific grip, not shown, set into the place on the tibia T, by occupying the same configuration for attachment to the tibia which was occupied by the tibia phantom 60.

Figure 15:
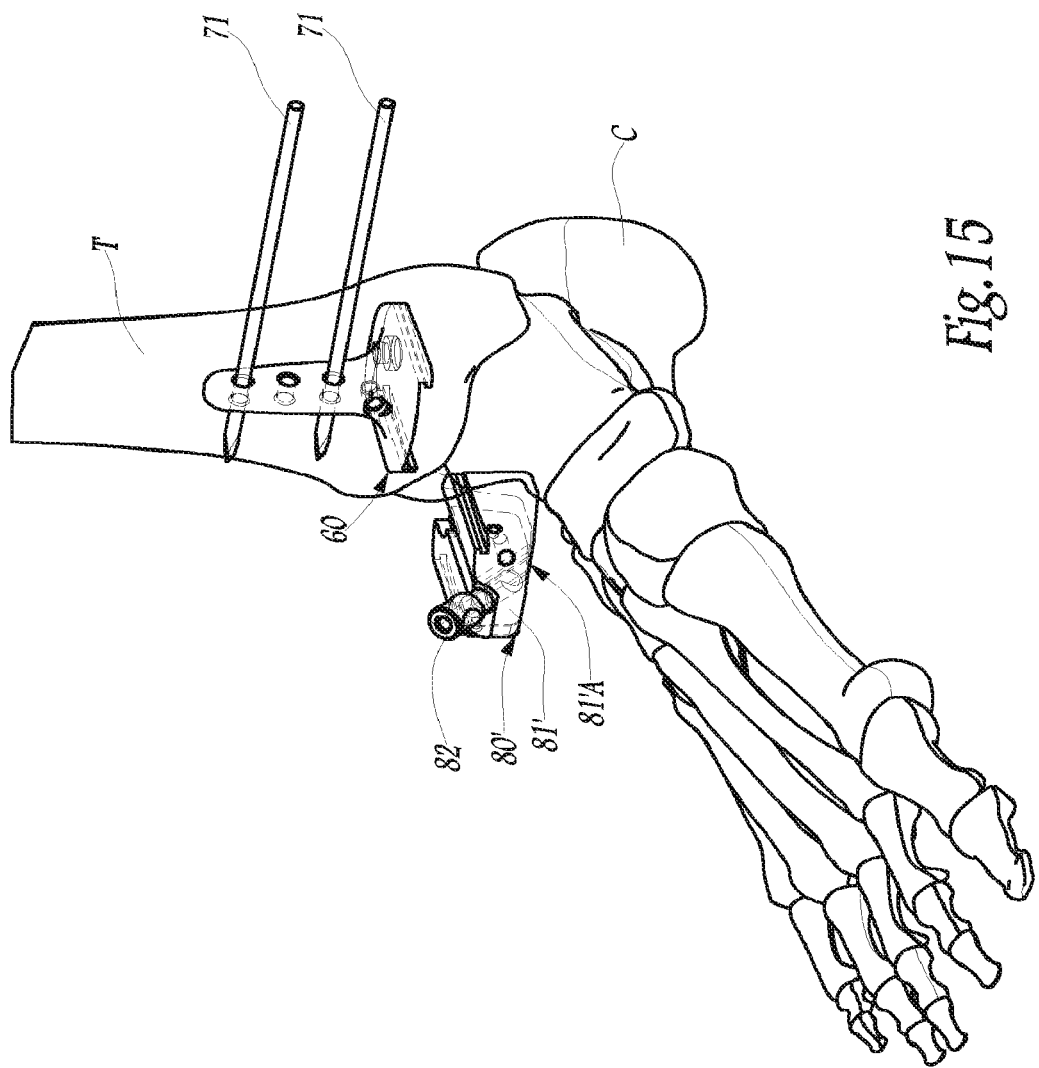
FIGS. 15, 16 and 17 are views similar to FIGS. 7, 9 and 10 respectively, illustrating an alternative instrumentation according to embodiments of the present invention.
Figure 16:
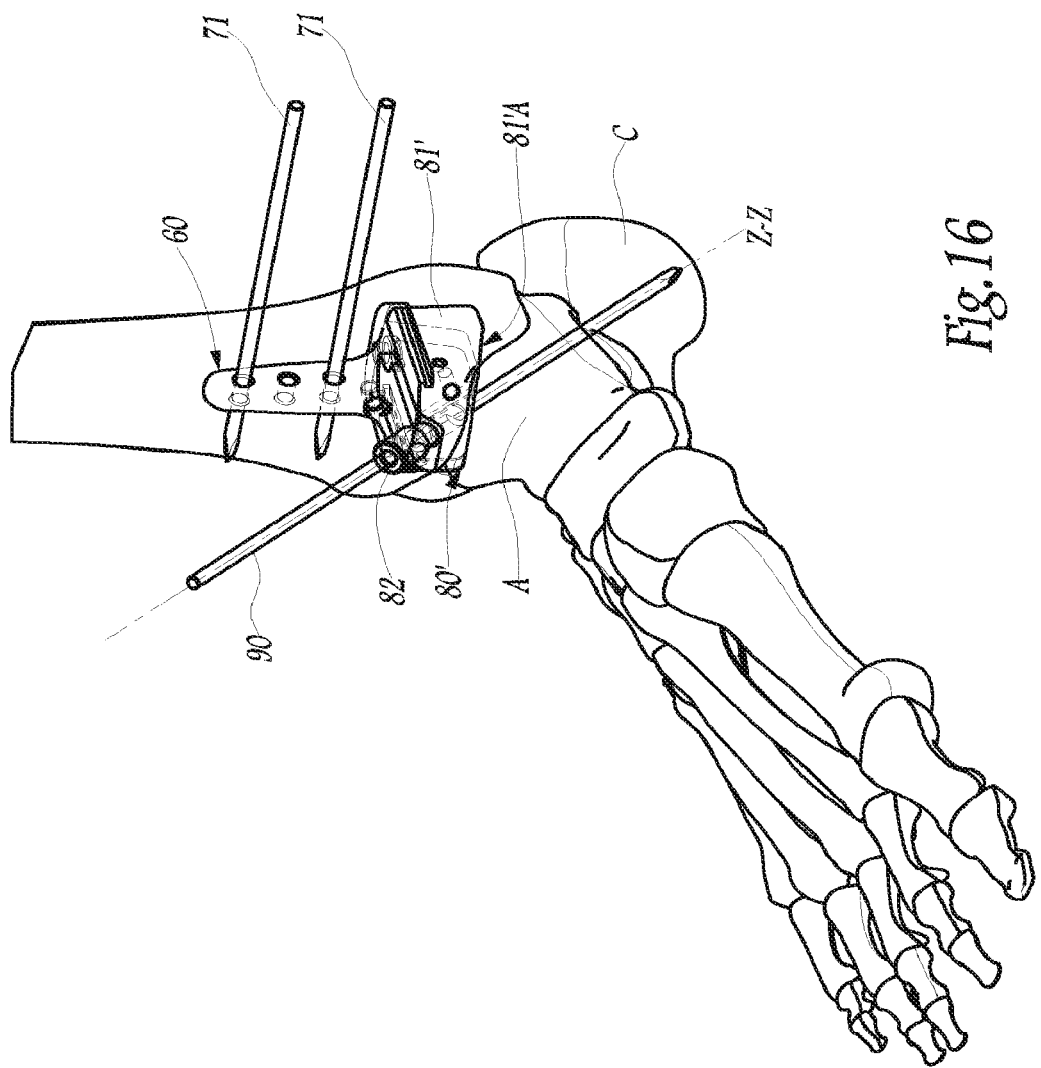
Figure 17:
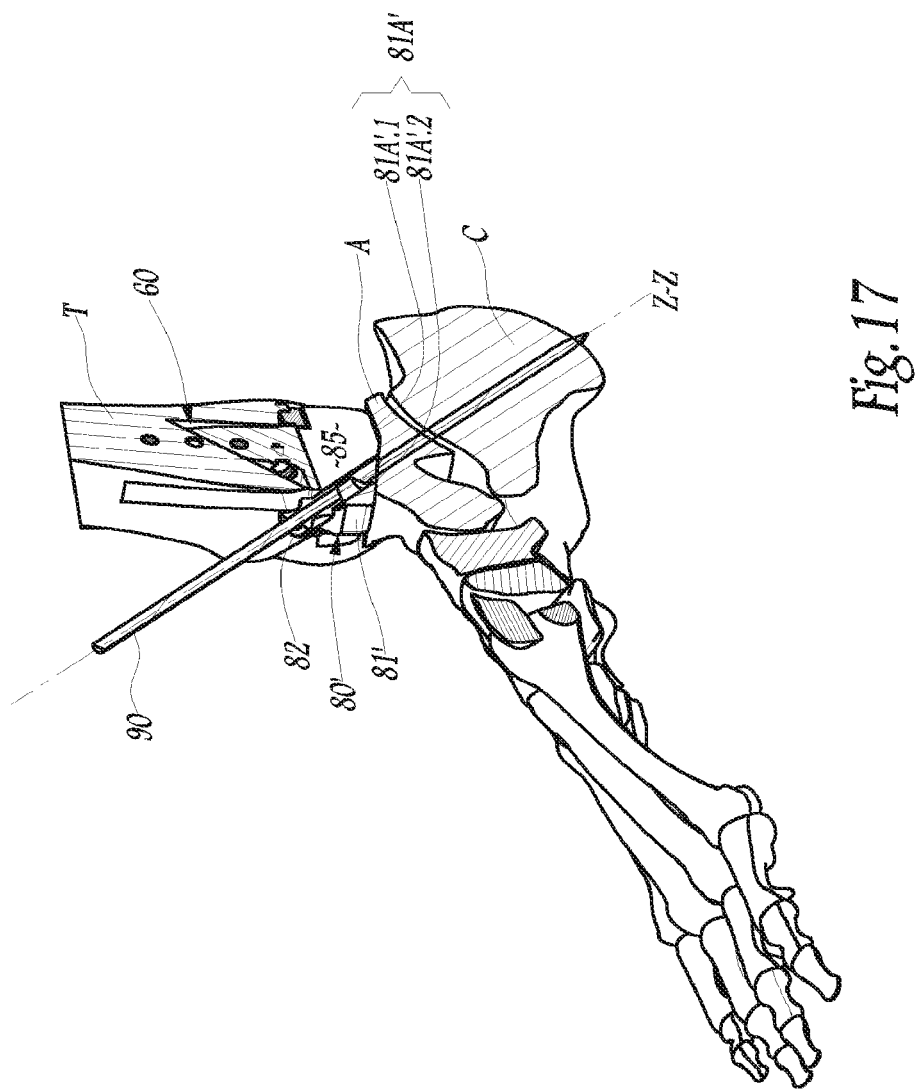

In FIGS. 15 to 17, an alternative of the surgical instrumentation is illustrated, which is only distinguished from the aforementioned instrumentation by its aiming guide, referenced as 80'. More specifically, as can be seen by comparing FIGS. 15, 16 and 17 with FIGS. 7, 9 and 10, the aiming guide 80' is identical with the aiming guide 80, except with respect to the lower side of its main body 81'. Also, in FIGS. 15 to 17, the components identical with the ones shown in FIGS. 7, 9 and 10 bear the same numerical references and will not be described here in more detail, as they are already described above.

Thus, unlike the body 81 of the aiming guide 80, which, on its lower side, delimits a substantially planar lower face 81A oriented along an antero-posterior direction, the body 81' of the aiming guide 80' has, on its lower side, a lower face 81A' with a globally beveled shape: in the exemplary embodiment considered in FIGS. 15 to 17, this lower face 81A' includes a posterior portion 81A'.1, which is substantially planar and oriented along an antero-posterior direction as well as anterior portion 81A'.2 which is substantially planar and which connects, in a tilted way relative to the antero-posterior direction, the posterior portion 81A'.1 and the anterior face of the body 81'. This difference in shape of the lower faces 81A and 81A' of the bodies 81 and 81' is related to considerations relating to the bone condition in which the talus A is found. Indeed, as explained above, the use of the aiming guide 80 assumes the presence of an upper sectional plane of the talus A, this upper sectional plane being either pre-existent in the setting into place of the ankle prosthesis 1, or specifically made by the surgeon at the beginning of the surgical operation aiming at implanting this ankle prosthesis 1. During the surgical operation, the surgeon easily causes cooperation by a plane-plane contact, of the aforementioned upper sectional plane of the talus A and of the lower face 81A of the body 81 of the aiming guide 80, notably with the purposes of adjusting their relative position, in particular during the placement of the talo-calcaneal pin 90. In the case when the talus A has an alteration such that making such an upper sectional plane is made impossible, notably from the fact of a necrosis or damage of the talus, the bone preparation of the talus is then performed by the surgeon at an anatomic level located closer to the calcaneus C, at the very least for the posterior portion of the talus, while the anterior portion of the talus is generally restored by a bone graft. The posterior portion 81A'.1 of the lower face 81A' of the body 81' of the aiming guide 80' may be caused to cooperate, along a plane-plane contact, with the residual rear portion of the talus A, or even directly with the calcaneus C in the case when the rear portion of the talus A is totally removed by the surgeon on the one hand and, the anterior portion 81A'.2 of this lower face 81A' may then be used by the surgeon for cooperating with the aforementioned bone graft, if necessary by having it rest against this graft so as to stabilize it, according to embodiments of the present invention.

Of course, for the embodiment of the instrumentation illustrated by FIGS. 15 to 17, the corresponding talus phantom, not shown in these figures, has its main block with a lower face geometrically similar to the lower face 81A' of the body 81', according to embodiments of the present invention.

More generally, as yet another alternative (not shown), the geometry of the lower faces of the body of the aiming guide and of the body of the talus phantom may be adapted to a particular bone preparation of the talus A, taking into account the condition of the bone material of the latter.

Various arrangements and alternatives to the surgical instrumentation described herein as well as to the method for using this instrumentation may moreover be used, either individually or in combinations of two or more. For example, embodiments other than the sliding link are possible for the mechanical link between the tibial phantom 60 and the aiming guide 80 or 80' from the moment that this mechanical link predetermines the relative positioning of the aiming guide and of the tibial phantom when the latter is attached to the tibia. Also, for example, after having set the pin 90 into place, in other words after the fourth operating step as described above, the surgeon may for various reasons wish to continue the operation by shifting the axis, along which the anchoring keel 22 of the talus implant 20 will be implanted at the end of the operation. To do this, the instrumentation includes an ad hoc shifting part, in the form of a block crossed by at least two holes parallel to each other; this shifting part is added onto the already implanted pin 90, by engaging the latter into one of the two aforementioned holes, while the other hole is then used by the surgeon for setting into place a second talo-calcaneal pin, similar to the pin 90; it is understood that this other talo-calcaneal pin then extends parallel to the pin 90, while being shifted relatively to the latter by the predetermined center line between both holes of the shifting part; as an extension of the foregoing considerations, an embodiment of this shifting part may include a barrel including several through-holes, structurally and functionally similar to the two aforementioned holes and distributed in a predetermined way relatively to each other. As yet another example, rather than using the pin 90, other functionally similar instrumentation elements may be used.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A surgical instrumentation assembly for positioning an ankle prosthesis, the instrumentation assembly comprising:
    an aiming guide, adapted for setting into place an instrumentation element through the talus and the calcaneus of the patient along an axis for implanting the talo-calcaneal anchoring keel;
    wherein said aiming guide defines a through-passage for receiving the instrumentation element, said through-passage positioned to disengage said aiming guide from the instrumentation element while leaving the instrumentation element in place through the talus and the calcaneus;
    wherein said aiming guide comprises a main body which defines said through-passage, wherein said through-passage is a slot which opens onto two opposing faces of said main body and onto at least one other face of said main body, and wherein said slot includes a first width distal said at least one other face of said main body and a second width proximal said at least one other face of said main body, wherein said first width is larger than said second width; and
    a piercing barrel removably attached to said main body while opening into said through-passage, said piercing barrel adapted for guiding the instrumentation element.

2. The surgical instrumentation assembly of claim 1, wherein said piercing barrel is received within a portion of said slot having said first width.

3. The surgical instrumentation assembly of claim 1, further comprising an instrumentation element positionable within said through-passage, wherein said instrumentation element has a width smaller than a portion of said slot having said second width.

4. The surgical instrumentation assembly of claim 1, further comprising at least one of a tibial phantom, a talus phantom, a prosthetic shoe, and a centering device.

5. The surgical instrumentation assembly of claim 4, further comprising said tibial phantom, wherein said tibial phantom and said aiming guide mechanically engage with each other to allow movement of said aiming guide with respect to said tibial phantom along an antero-posterior direction and restrict movement of said tibial phantom and said aiming guide relative to each other along vertical and medio-lateral directions so as to permit disengagement of said aiming guide from said tibial phantom while leaving the instrumentation element in place.

6. The surgical instrumentation assembly of claim 5, wherein said tibial phantom and said aiming guide mechanically engage with each other using one or more corresponding sliding engagements.

7. The surgical instrumentation assembly of claim 1, in combination with a tibia implant and a talus implant provided with a talo-calcaneal anchoring keel.

8. The surgical instrumentation assembly of claim 1, wherein said aiming guide comprises a visual indicator configured to facilitate positioning of said aiming guide relative to a specific anatomic location of the talus.

9. The surgical instrumentation assembly of claim 8, wherein said specific anatomic location of the talus is the talonavicular joint.

10. A surgical instrumentation assembly for positioning an ankle prosthesis, the instrumentation assembly comprising:
an aiming guide, adapted for setting into place an instrumentation element through the talus and the calcaneus of the patient along an axis for implanting the talo-calcaneal anchoring keel;
wherein said aiming guide defines a through-passage for receiving the instrumentation element, said through-passage positioned to disengage said aiming guide from the instrumentation element while leaving the instrumentation element in place through the talus and the calcaneus;
wherein said aiming guide comprises a main body which defines said through-passage, wherein said through-passage is a slot which opens onto two opposing faces of said main body and onto at least one other face of said main body, and wherein said slot includes a first width distal said at least one other face of said main body and a second width proximal said at least one other face of said main body, wherein said first width is larger than said second width; and
an instrumentation element positionable within said through-passage, wherein said instrumentation element has a width smaller than a portion of said slot having said second width.

11. The surgical instrumentation assembly of claim 10, further comprising a piercing barrel removably attached to said main body while opening into said through-passage, said piercing barrel adapted for guiding the instrumentation element and wherein said piercing barrel is received within a portion of said slot having said first width.

12. The surgical instrumentation assembly of claim 10, further comprising at least one of a tibial phantom, a talus phantom, a prosthetic shoe, and a centering device.

13. The surgical instrumentation assembly of claim 12, further comprising said tibial phantom, wherein said tibial phantom and said aiming guide mechanically engage with each other to allow movement of said aiming guide with respect to said tibial phantom along an antero-posterior direction and restrict movement of said tibial phantom and said aiming guide relative to each other along vertical and medio-lateral directions so as to permit disengagement of said aiming guide from said tibial phantom while leaving the instrumentation element in place.

14. The surgical instrumentation assembly of claim 13, wherein said tibial phantom and said aiming guide mechanically engage with each other using one or more corresponding sliding engagements.

15. The surgical instrumentation assembly of claim 10, in combination with a tibia implant and a talus implant provided with a talo-calcaneal anchoring keel.

16. The surgical instrumentation assembly of claim 10, wherein said aiming guide comprises a visual indicator configured to facilitate positioning of said aiming guide relative to a specific anatomic location of the talus.

17. The surgical instrumentation assembly of claim 16, wherein said specific anatomic location of the talus is the talonavicular joint.

18. A surgical instrumentation assembly for positioning an ankle prosthesis, the instrumentation assembly comprising:
an aiming guide, adapted for setting into place an instrumentation element through the talus and the calcaneus of the patient along an axis for implanting the talo-calcaneal anchoring keel;
wherein said aiming guide defines a through-passage for receiving the instrumentation element, said through-passage positioned to disengage said aiming guide from the instrumentation element while leaving the instrumentation element in place through the talus and the calcaneus;
wherein said aiming guide comprises a main body which defines said through-passage, wherein said through-passage is a slot which opens onto two opposing faces of said main body and onto at least one other face of said main body;
at least one of a tibial phantom, a talus phantom, a prosthetic shoe, and a centering device; and
wherein said tibial phantom and said aiming guide mechanically engage with each other to allow movement of said aiming guide with respect to said tibial phantom along an antero-posterior direction and restrict movement of said tibial phantom and said aiming guide relative to each other along vertical and medio-lateral directions so as to permit disengagement of said aiming guide from said tibial phantom while leaving the instrumentation element in place.

19. The surgical instrumentation assembly of claim 18, wherein said tibial phantom and said aiming guide mechanically engage with each other using one or more corresponding sliding engagements.

20. The surgical instrumentation assembly of claim 18, wherein said slot includes a first width distal said at least one other face of said main body and a second width proximal said at least one other face of said main body, wherein said first width is larger than said second width.

21. The surgical instrumentation assembly of claim 20, further comprising a piercing barrel removably attached to said main body while opening into said through-passage, said piercing barrel adapted for guiding the instrumentation element, and wherein said piercing barrel is received within a portion of said slot having said first width.

22. The surgical instrumentation assembly of claim 18, in combination with a tibia implant and a talus implant provided with a talo-calcaneal anchoring keel.

23. The surgical instrumentation assembly of claim 18, wherein said aiming guide comprises a visual indicator configured to facilitate positioning of said aiming guide relative to a specific anatomic location of the talus.

24. The surgical instrumentation assembly of claim 23, wherein said specific anatomic location of the talus is the talonavicular joint.

* * * * *